US010538745B2

(12) United States Patent
Liu et al.

(10) Patent No.: US 10,538,745 B2
(45) Date of Patent: Jan. 21, 2020

(54) KEY PHOSPHORYLATION SITE OF TEMPERATURE SENSITIVITY OF INFLUENZA A VIRUS AND USE THEREOF

(71) Applicant: Institute of Microbiology, Chinese Academy of Sciences, Beijing (CN)

(72) Inventors: Wenjun Liu, Beijing (CN); Weinan Zheng, Beijing (CN); Jing Li, Beijing (CN)

(73) Assignee: Institute of Microbiology, Chinese Academy of Sciences, Beijing (CN)

( * ) Notice: Subject to any disclaimer, the term of this patent is extended or adjusted under 35 U.S.C. 154(b) by 0 days.

(21) Appl. No.: 16/085,469

(22) PCT Filed: Jan. 22, 2017

(86) PCT No.: PCT/CN2017/072063
§ 371 (c)(1),
(2) Date: Sep. 14, 2018

(87) PCT Pub. No.: WO2018/129767
PCT Pub. Date: Jul. 19, 2018

(65) Prior Publication Data
US 2019/0085302 A1 Mar. 21, 2019

(30) Foreign Application Priority Data
Jan. 16, 2017 (CN) .......................... 2017 1 0028543

(51) Int. Cl.
*C12N 7/00* (2006.01)
*C07K 14/005* (2006.01)
*A61K 39/00* (2006.01)

(52) U.S. Cl.
CPC .............. *C12N 7/00* (2013.01); *C07K 14/005* (2013.01); *A61K 39/00* (2013.01); *C12N 2760/16121* (2013.01); *C12N 2760/16122* (2013.01); *C12N 2760/16134* (2013.01)

(58) Field of Classification Search
None
See application file for complete search history.

(56) References Cited

FOREIGN PATENT DOCUMENTS

| CN | 104592367 A | 5/2015 |
|---|---|---|
| WO | WO 2016/172588 A1 | 10/2016 |

OTHER PUBLICATIONS

Yu et al., Identification and Characterization of Three Novel Nuclear Export Signals in the Influenza A Virus Nucleoprotein, 2012, Journal of Virology, vol. 86, No. 9, pp. 4970-4980.*
Li, Z. et al. 2009 "Mutational Analysis of Conserved Amino Acids in the Influenza A Virus Nucleoprotein" *Journal of Virology* 83: 4153-4162.
Wang, Z. et al. 2010 "Development of influenza virus PR8 mutants and their characteristics on embryonated chicken eggs" Chinese Veterinary Science, 40(8): 788-792.

* cited by examiner

*Primary Examiner* — Benjamin P Blumel
(74) *Attorney, Agent, or Firm* — Knobbe, Martens, Olson & Bear LLP

(57) ABSTRACT

A recombinant virus is obtained by mutating a codon that encodes a tyrosine residue at position 385 of NP protein in the genome of influenza A virus to a codon of phenylalanine residue. The virus WSN-Y385F is a temperature-sensitive virus that can normally replicate and survive at 37° C., and cannot normally replicate and cannot survive at 33° C. Phosphorylation of a NP protein of influenza A virus can be inhibited by mutating an amino acid residue at position 385 from N terminal of the NP protein of influenza A virus, from a tyrosine to a phenylalanine. The recombinant virus can be used in analyzing mechanisms of infection by influenza virus, and in connection with methods of prevention and treatment of infection by influenza virus.

11 Claims, 5 Drawing Sheets
Specification includes a Sequence Listing.

A

B

A

B

SEQUENCE LISTING

```
<160> NUMBER OF SEQ ID NOS: 16

<210> SEQ ID NO 1
<211> LENGTH: 498
<212> TYPE: PRT
<213> ORGANISM: Influenza A

<400> SEQUENCE: 1

Met Ala Thr Lys Gly Thr Lys Arg Ser Tyr Glu Gln Met Glu Thr Asp
1               5                   10                  15
```

-continued

Gly Glu Arg Gln Asn Ala Thr Glu Ile Arg Ala Ser Val Gly Lys Met
                20                  25                  30

Ile Asp Gly Ile Gly Arg Phe Tyr Ile Gln Met Cys Thr Glu Leu Lys
            35                  40                  45

Leu Ser Asp Tyr Glu Gly Arg Leu Ile Gln Asn Ser Leu Thr Ile Glu
 50                  55                  60

Arg Met Val Leu Ser Ala Phe Asp Glu Arg Arg Asn Lys Tyr Leu Glu
 65                  70                  75                  80

Glu His Pro Ser Ala Gly Lys Asp Pro Lys Lys Thr Gly Gly Pro Ile
                 85                  90                  95

Tyr Arg Arg Val Asp Gly Lys Trp Arg Arg Glu Leu Ile Leu Tyr Asp
                100                 105                 110

Lys Glu Glu Ile Arg Arg Ile Trp Arg Gln Ala Asn Asn Gly Asp Asp
                115                 120                 125

Ala Thr Ala Gly Leu Thr His Met Met Ile Trp His Ser Asn Leu Asn
130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
                180                 185                 190

Leu Ile Arg Met Ile Lys Arg Gly Ile Asn Asp Arg Asn Phe Trp Arg
                195                 200                 205

Gly Glu Asn Gly Arg Arg Thr Arg Ile Ala Tyr Glu Arg Met Cys Asn
                210                 215                 220

Ile Leu Lys Gly Lys Phe Gln Thr Ala Ala Gln Arg Thr Met Val Asp
225                 230                 235                 240

Gln Val Arg Glu Ser Arg Asn Pro Gly Asn Ala Glu Phe Glu Asp Leu
                245                 250                 255

Ile Phe Leu Ala Arg Ser Ala Leu Ile Leu Arg Gly Ser Val Ala His
                260                 265                 270

Lys Ser Cys Leu Pro Ala Cys Val Tyr Gly Ser Ala Val Ala Ser Gly
                275                 280                 285

Tyr Asp Phe Glu Arg Glu Gly Tyr Ser Leu Val Gly Ile Asp Pro Phe
                290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Lys Val
                340                 345                 350

Val Pro Arg Gly Lys Leu Ser Thr Arg Gly Val Gln Ile Ala Ser Asn
                355                 360                 365

Glu Asn Met Glu Thr Met Glu Ser Ser Thr Leu Glu Leu Arg Ser Arg
                370                 375                 380

Tyr Trp Ala Ile Arg Thr Arg Ser Gly Gly Asn Thr Asn Gln Gln Arg
385                 390                 395                 400

Ala Ser Ser Gly Gln Ile Ser Ile Gln Pro Thr Phe Ser Val Gln Arg
                405                 410                 415

Asn Leu Pro Phe Asp Arg Pro Thr Ile Met Ala Ala Phe Thr Gly Asn
                420                 425                 430

Thr Glu Gly Arg Thr Ser Asp Met Arg Thr Glu Ile Ile Arg Leu Met
            435                 440                 445

Glu Ser Ala Arg Pro Glu Asp Val Ser Phe Gln Gly Arg Gly Val Phe
        450                 455                 460

Glu Leu Ser Asp Glu Lys Ala Thr Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 2
<211> LENGTH: 984
<212> TYPE: DNA
<213> ORGANISM: Artificial Sequence
<220> FEATURE:
<223> OTHER INFORMATION: plasmid pHH21-M

<400> SEQUENCE: 2

```
atgagtcttc taaccgaggt cgaaacgtac gttctctcta tcgtcccgtc aggccccctc      60
aaagccgaga tcgcacagag acttgaagat gtctttgcag gaagaacac cgatcttgag      120
gttctcatgg aatggctaaa gacaagacca atcctgtcac ctctgactaa ggggatttta    180
ggatttgtgt tcacgctcac cgtgcccagt gagcgggac tgcagcgtag acgctttgtc    240
caaaatgctc ttaatgggaa cggagatcca ataacatgg acaaagcagt taactgtat    300
aggaagctta agagggagat aacattccat ggggccaaag aaatagcact cagttattct    360
gctggtgcac ttgccagttg tatgggcctc atatacaaca ggatggggc tgtgaccact    420
gaagtggcat ttggcctggt atgcgcaacc tgtgaacaga ttgctgactc ccagcatcgg    480
tctcataggc aaatggtgac aacaccaat ccactaatca gacatgagaa cagaatggtt      540
ctagccagca ctacagctaa ggctatggag caaatggctg gatcgagtga gcaagcagca    600
gaggccatgg atattgctag tcaggccagg caaatggtgc aggcgatgag aaccgttggg    660
actcatccta gctccagtgc tggtctaaaa gatgatcttc ttgaaaattt gcaggcctat    720
cagaaacgaa tggggtgca gatgcaacga ttcaagtgat cctctcgtca ttgcagcaaa    780
tatcattgga atcttgcact tgatattgtg gattcttgat cgtctttttt tcaaatgcat    840
ttatcgtcgc tttaaatacg gtttgaaaag agggccttct acggaaggag tgccagagtc    900
tatgagggaa gaatatcgaa aggaacagca gaatgctgtg gatgttgacg atggtcattt    960
tgtcaacata gagctggagt aaaa                                              984
```

<210> SEQ ID NO 3
<211> LENGTH: 2202
<212> TYPE: DNA
<213> ORGANISM: Artificial Sequence
<220> FEATURE:
<223> OTHER INFORMATION: plasmid pcDNA3.0-PA

<400> SEQUENCE: 3

```
ctgattcaaa atggaagatt ttgtgcgaca atgcttcaat ccgatgattg tcgagcttgc      60
ggaaaaggca atgaaagagt atggagagga cctgaaaatc gaaacaaaca atttgcagc    120
aatatgcact cacttggaag tgtgcttcat gtattcagat tttcacttca tcgatgagca    180
aggcgagtca atagtcgtag aacttggcga tccaaatgca cttttgaagc acagatttga    240
aataatcgag ggaagagatc gcacaatagc ctggacagta taaacagta tttgcaacac    300
tacaggggct gagaaaccaa agtttctacc agatttgtat gattacaaga gaatagatt    360
```

```
catcgaaatt ggagtaacaa ggagagaagt tcacatatac tatctgggaaa aggccaataa    420 aattaaatct gagaagacac acatccacat tttctcattc actggggagg aaatggccac    480
aaaggccgac tacactctcg atgaagaaag cagggctagg atcaaaacca ggctattcac    540
cataagacaa gaaatggcta gcagaggcct ctgggattcc tttcgtcagt ccgagagagg    600
cgaagagaca attgaagaaa gatttgaaat cacaggaaca atgcgcaagc ttgccgacca    660
aagtctcccg ccaaacttct ccagccttga aaattttaga gcctatgtgg atggattcga    720
accgaacggc tacattgagg gcaagctttc tcaaatgtcc aaagaagtaa atgctagaat    780 tgaaccttt  ttgaaatcaa caccacgacc acttagactt ccggatgggc ctccctgttc    840
tcagcggtcc aaattcctgc tgatggatgc cttaaaatta agcattgagg acccaagtca    900
tgagggagag gggataccgc tatatgatgc aatcaaatgc atgagaacat tctttggatg    960
gaaggaaccc aatgttgtta aaccacacga aagggaata  aatccaaatt atcttctgtc   1020
atggaagcaa gtactggcag aactgcagga cattgagaat gaggagaaaa ttccaaggac   1080
taaaaatatg aagaaaacga gtcagttaaa gtgggcactt ggtgagaaca tggcaccaga   1140
aaaggtagac tttgacgatt gtaaagatgt aggcgatttg aagcaatatg atagtgatga   1200
accagaattg aggtcgcttg caagttggat tcagaatgag ttcaacaagg catgtgaact   1260
gaccgattca agctgatag  agctcgatga gattggagaa gatgcggctc caattgaaca   1320
cattgcaagc atgagaagga attatttcac agcagaggtg tctcattgca gagccacaga   1380
atacataatg aaggggggtgt acatcaatac tgccttgctt aatgcatcct gtgcagcaat   1440
ggatgatttc caattgattc caatgataag caagtgtaga actaaggagg aaggcgaaa    1500 gaccaatttg tacggtttca tcataaaagg aagatcccac ttaaggaatg acaccgatgt   1560
ggtaaacttt gtgagcatgg agttttccct cactgaccca agacttgaac cacacaaatg   1620
ggagaagtac tgtgttcttg aggtaggaga tatgcttcta agaagtgcca taggccatgt   1680
gtcaaggcct atgttcttgt atgtgaggac aaatggaacc tcaaaaatta aaatgaaatg   1740
ggggatggaa atgaggcgtt gcctccttca gtcacttcaa caaatcgaga gtatgattga   1800
agctgagtcc tctgtcaagg agaaagacat gaccaaagag ttctttgaaa acaaatcaga   1860
acatggcccc gttggagagt cccccaaagg agtggaggaa ggttccattg gaaggtctg    1920 cagaaccttta ttggcaaagt cggtattcaa cagcttgtat gcatctccac aactggaagg   1980 atttttcagct gaatcaagaa aactgcttct tatcgttcag gctcttaggg acaacctgga   2040
acctgggacc tttgatcttg gggggctata tgaagcaatt gaggagtgcc tgattaatga   2100
tcctggggtt ttgcttaatg cttcttggtt caactccttc ctcacacatg cattgagata   2160
gttgtggcaa tgctactatt tgctatccat actgtccaaa aa                       2202
```

<210> SEQ ID NO 4
<211> LENGTH: 2303
<212> TYPE: DNA
<213> ORGANISM: Artificial Sequence
<220> FEATURE:
<223> OTHER INFORMATION: plasmid pcDNA3.0-PBI

<400> SEQUENCE: 4

```
atttgaatgg atgtcaatcc gactttactt ttcttaaaag tgccagcaca aaatgctata     60
agcacaactt tcccttatac tggagaccct ccttacagcc atgggacagg aacaggatac    120
accatggata ctgtcaacag gacacatcag tactcagaaa ggggaagatg gacaacaaac    180
```

```
accgaaactg gagcaccgca actcaacccg attgatgggc cactgccaga agacaatgaa      240
ccaagtggtt atgcccaaac agattgtgta ttggaagcaa tggccttcct tgaggaatcc      300
catcctggta tctttgagac ctcgtgtctt gaaacgatgg aggttgttca gcaaacacga      360
gtggacaagc tgacacaagg ccgacagacc tatgactgga ctctaaatag gaaccagcct      420
gctgcaacag cattggccaa cacaatagaa gtgttcagat caaatggcct cacggccaat      480
gaatctggaa ggctcataga cttccttaag gatgtaatgg agtcaatgaa caaagaagaa      540
atggagatca caactcattt tcagagaaag agacgagtga gagacaatat gactaagaaa      600
atggtgacac agagaacaat aggtaaaagg aagcagagat gaacaaaag gagttatcta      660 attagggcat taaccctgaa cacaatgacc aaagatgctg agagagggaa gctaaaacgg      720
agagcaattg caaccccagg gatgcaaata aggggggtttg tatactttgt tgagacacta      780
gcaaggagta tatgtgagaa acttgaacaa tcaggattgc cagttggagg caatgagaag      840
aaagcaaagt tggcaaatgt tgtaaggaag atgatgacca attctcagga cactgaaatt      900
tctttcacca tcactggaga taacaccaaa tggaacgaaa atcagaaccc tcggatgttt      960
ttggccatga tcacatatat aaccagaaat cagcccgaat ggttcagaaa tgttctaagt     1020
attgctccaa taatgttctc aaacaaaatg gcgagactgg gaaaggggta catgtttgag     1080
agcaagagta tgaaacttag aactcaaata cctgcagaaa tgctagcaag catcgatttg     1140
aaatacttca atgattcaac tagaaagaag attgaaaaaa tccggccgct cttaatagat     1200
gggactgcat cattgagccc tggaatgatg atgggcatgt tcaatatgtt aagtactgta     1260
ttaggcgtct ccatcctgaa tcttggacaa aagagacaca ccaagactac ttactggtgg     1320
gatggtcttc aatcttctga tgattttgct ctgattgtga atgcacccaa tcatgaaggg     1380
attcaagccg gagtcaacag gttttatcga acctgtaagc tacttggaat taatatgagc     1440
aagaaaaagt cttacataaa cagaacaggt acatttgaat tcacaagttt tttctatcgt     1500
tatgggtttg ttgccaattt cagcatggag cttcccagct tggggtgtc tgggatcaac     1560 gagtctgcgg acatgagtat tggagttact gtcatcaaaa acaatatgat aaacaatgat     1620
cttggtccag caaccgctca aatggcccctt cagctgttca tcaaagatta caggtacacg     1680
taccggtgcc atagaggtga cacacaaata caaacccgaa gatcatttga aataaagaaa     1740
ctgtgggagc aaacccattc caaagctgga ctgctggtct ccgacggagg cccaaattta     1800
tacaacatta gaaatctcca cattcctgaa gtctgcttga atgggaatt aatggatgag     1860 gattaccagg gcgtttatg caacccactg aacccatttg tcaaccataa agacattgaa     1920
tcagtgaaca atgcagtgat aatgccagca catggtccag ccaaaaacat ggagtatgat     1980
gctgttgcaa caacacactc ctggatcccc aaaagaaatc gatccatctt gaatacaagc     2040
caaagaggaa tacttgaaga tgaacaaatg taccaaaagt gctgcaactt attgaaaaa     2100 ttcttcccca gcagttcata cagaagacca gtcgggatat ccagtatggt ggaggctatg     2160
gtttccagag cccgaattga tgcacgaatt gatttcgaat ctggaaggat aaagaaagag     2220
gagttcactg agatcatgaa gatctgttcc accattgaag agctcagacg gcaaaaatag     2280
tgaatttagc ttgtccttca tga                                            2303

<210> SEQ ID NO 5
<211> LENGTH: 2290
<212> TYPE: DNA
<213> ORGANISM: Artificial Sequence
<220> FEATURE:
<223> OTHER INFORMATION: plasmid pHH21-PB2
```

<400> SEQUENCE: 5

```
atggaaagaa taaaagaact aaggaatcta atgtcgcagt ctcgcactcg cgagatactc    60
acaaaaacca ccgtggacca tatggccata atcaagaagt acacatcagg aagacaggag   120
aagaacccag cacttaggat gaaatggatg atggcaatga aatatccaat tacagcagac   180
aagaggataa cggaaatgat tcctgagaga aatgagcagg acaaactttt atggagtaaa   240
atgaatgacg ccggatcaga ccgagtgatg gtatcacctc tggctgtgac atggtggaat   300
aggaatggac cagtgacaag tacagttcat tatccaaaaa tctacaaaac ttatttgaa    360
aaagtcgaaa ggttaaaaca tggaaccttt ggccctgtcc attttagaaa ccaagtcaaa   420
atacgtcgaa gagttgacat aaatcctggt catgcagatc tcagtgccaa agaggcacag   480
gatgtaatca tggaagttgt tttccctaac gaagtgggag ccaggatact aacatcggaa   540
tcgcaactaa cgacaaccaa agagaagaaa gaagaactcc agggttgcaa aatttctcct   600
ctgatggtgg catacatgtt ggagagagaa ctggtccgca aaacgagatt cctcccagtg   660
gctggtggaa caagcagtgt gtacattgaa gtgttgcatt tgacccaagg aacatgctgg   720
gaacagatgt acactccagg aggggaggcg aggaatgatg atgttgatca aagcttaatt   780
attgctgcta gaaacatagt aagaagagcc acagtatcag cagatccact agcatcttta   840
ttggagatgt gccacagcac gcagattggt ggagtaagga tggtaaacat ccttaggcag   900
aacccaacag aagagcaagc cgtggatatt tgcaaggctg caatgggact gagaattagc   960
tcatccttca gttttggtgg attcacattt aagagaacaa gcggatcatc agtcaagaga  1020
gaggaagagg tgcttacggg caatcttcag acattgaaga taagagtgca tgagggatat  1080
gaagagttca caatggttgg gagaagagca acagctatac tcagaaaagc aaccaggaga  1140
ttgattcagc tgatagtgag tgggagagac gaacagtcga ttgccgaagc aataattgtg  1200
gccatggtat tttcacaaga ggattgtatg ataaaagcag ttagaggtga cctgaatttc  1260
gtcaataggg cgaatcagcg attgaatccc atgcaccaac ttttgagaca ttttcagaag  1320
gatgcaaagg tgctctttca aaattgggga attgaatcca tcgacaatgt gatgggaatg  1380
atcgggatat tgcccgacat gactccaagc accgagatgt caatgagagg agtgagaatc  1440
agcaaaatgg gggtagatga gtattccagc gcggagaaga tagtggtgag cattgaccgt  1500
tttttgagag ttagggacca acgtgggaat gtactactgt ctcccgagga ggtcagtgaa  1560
acacagggaa cagagaaact gacaataact tactcatcgt caatgatgtg ggagattaat  1620
ggtcctgaat cagtgttggt caataccat cagtggatca tcagaaactg ggaaactgtt  1680
aaaattcagt ggtcccagaa tcctacaatg ctgtacaata aaatggaatt tgagccattt  1740
cagtctttag ttccaaaggc cgttagaggc caatacagtg ggtttgtgag aactctgttc  1800
caacaaatga gggatgtgct tgggacattt gataccgctc agataataaa acttcttccc  1860
ttcgcagccg ctccaccaaa gcaaagtgga atgcagttct cctcattgac tataaatgtg  1920
aggggatcag gaatgagaat acttgtaagg ggcaattctc cagtattcaa ctacaacaag  1980
accactaaaa gactcacagt tctcggaaag gatgctggcc cttaactga agacccagat  2040
gaaggcacag ctggagttga gtccgcagtt ctgagaggat tcctcattct gggcaaagaa  2100
gacaggagat atggaccagc attaagcata aatgaactga gcaaccttgc gaaaggagag  2160
aaggctaatg tgctaattgg gcaaggagac gtggtgttgg taatgaaacg gaaacggaac  2220
tctagcatac ttactgacag ccagacagcg accaaaagaa ttcggatggc catcaattag  2280
```
tgtcgaatag                                                                        2290

<210> SEQ ID NO 6
<211> LENGTH: 1725
<212> TYPE: DNA
<213> ORGANISM: Artificial Sequence
<220> FEATURE:
<223> OTHER INFORMATION: plasmid pHH21-HA

<400> SEQUENCE: 6
ccaaaatgaa ggcaaaacta ctggtcctgt tatatgcatt tgtagctaca gatgcagaca     60
caatatgtat aggctaccat gcgaacaact caaccgacac tgttgacaca atattcgaga    120
agaatgtggc agtgacacat tctgttaacc tgctcgaaga cagacacaac gggaaactat    180
gtaaattaaa aggaatagcc ccactacaat tggggaaatg taacatcatc ggatggctct    240
tgggaaatcc agaatgcgac tcactgcttc cagcgagatc atggtcctac attgtagaaa    300
caccaaactc tgagaatgga gcatgttatc caggagattt catcgactat gaggaactga    360
gggagcaatt gagctcagta tcatcattag aaagattcga atatttccc aaggaaagtt     420
catggcccaa ccacacattc aacggagtaa cagcatcatg ctcccatagg ggaaaaagca    480
gtttttacag aaatttgcta tggctgacga agaaggggga ttcatcccca agctgacca    540
attcctatgt gaacaataaa gggaagaag tccttgtact atggggtgtt catcacccgt     600
ctagcagtga tgagcaacag agtctctata gtaatgaaa tgcttatgtc tctgtagcgt     660
cttcaaatta taacaggaga ttcacccccgg aaatagctgc aaggcccaaa gtaaagatc    720
aacatgggag gatgaactat tactggacct tgctagaacc cggagacaca ataatatttg    780
aggcaactgg taatctaata gcaccatggt atgctttcgc actgagtaga gggtttgagt    840
ccggcatcat cacctcaaac gcgtcaatgc atgagtgtaa cacgaagtgt caaacacccc    900
agggatctat aaacagcaat ctcccttcc agaatataca cccagtcaca ataggagagt     960
gcccaaaata tgtcaggagt accaaattga ggatggttac aggactaaga aacatcccat   1020
ccattcaata cagaggtcta tttggagcca ttgctggttt tattgagggg ggatggactg   1080
gaatgataga tggatggtat ggttatcatc atcagaatga acagggatca ggctatgcag   1140
cggatcaaaa aagcacacag aatgccatta acgggattac aaacaaggtg aactctatta   1200
tcgagaaaat gaacactcaa ttcacagctg tgggtaaaga attcaacaac ttagaaaaaa   1260
ggatggaaaa tttaaataaa aaagttgatg atgggttcct ggacatttgg acatataatg   1320
cagaattgtt agttctactg gaaaatggaa gaactttgga tttccatgac ttaaatgtga   1380
agaatctgta cgagaaagta aaaagccaat taaagaataa tgccaaagaa atcggaaatg   1440
ggtgttttga gttctaccac aagtgtgaca atgaatgcat ggaaagtgta agaaatggga   1500
cttatgatta tccaaaatat tcagaagaat caaagttgaa cagggaaaag atagatggag   1560
tgaaattgga atcaatgggg gtgtatcaga ttctggcgat ctactcaact gtcgccagtt   1620
cactggtgct tttggtctcc ctgggggcaa tcagtttctg gatgtgttct aatgggtctt   1680
tgcagtgcag aatatgcatc tgagattagg atttcagaaa tataa                   1725

<210> SEQ ID NO 7
<211> LENGTH: 1526
<212> TYPE: DNA
<213> ORGANISM: Artificial Sequence
<220> FEATURE:
<223> OTHER INFORMATION: plasmid pHH21-NP

<400> SEQUENCE: 7

| | |
|---|---:|
| tcactcacag agtgacatcg aaatcatggc gaccaaaggc accaaacgat cttacgaaca | 60 |
| gatggagact gatggagaac gccagaatgc cactgaaatc agagcatctg tcggaaaaat | 120 |
| gattgatgga attggacgat tctacatcca aatgtgcacc gaacttaaac tcagtgatta | 180 |
| tgagggacgg ctgattcaga acagcttaac aatagagaga atggtgctct ctgcttttga | 240 |
| cgagaggagg aataaatatc tagaagaaca tcccagtgcg gggaaagatc taagaaaac | 300 |
| tggaggacct atatacagga gagtagatgg aaagtggagg agagaactca tcctttatga | 360 |
| caaagaagaa ataagacgaa tctggcgcca agctaataat ggtgacgatg caacggctgg | 420 |
| tctgactcac atgatgatct ggcactccaa tttgaatgat gcaacttacc agaggacaag | 480 |
| agctcttgtt cgcacaggaa tggatcccag gatgtgctca ctgatgcagg gttcaaccct | 540 |
| ccctaggagg tctggggccg caggtgctgc agtcaaagga gttggaacaa tggtgatgga | 600 |
| attgatcaga atgatcaaac gtgggatcaa tgatcggaac ttctggaggg gtgagaatgg | 660 |
| acggagaaca aggattgctt atgaaagaat gtgcaacatt ctcaaaggga aatttcaaac | 720 |
| agctgcacaa agaacaatgg tggatcaagt gagagagagc cggaatccag aaatgctga | 780 |
| gttcgaagat ctcatctttt tagcacggtc tgcactcata ttgagagggt cagttgctca | 840 |
| caagtcctgc ctgcctgcct gtgtgtatgg atctgccgta ccagtggat acgactttga | 900 |
| aagagaggga tactctctag tcggaataga cccctttcaga ctgcttcaaa acagccaagt | 960 |
| atacagccta atcagaccaa atgagaatcc agcacacaag agtcaactgg tgtggatggc | 1020 |
| atgccattct gctgcatttg aagatctaag agtatcaagc ttcatcagag ggacgaaagt | 1080 |
| ggtcccaaga gggaagcttt ccactagagg agttcaaatt gcttccaatg aaaacatgga | 1140 |
| gactatggaa tcaagtaccc ttgaactgag aagcagatac tgggccataa ggaccagaag | 1200 |
| tggagggaac accaatcaac agagggcttc ctcgggccaa atcagcatac aacctacgtt | 1260 |
| ctcagtacag agaaatctcc cttttgacag accaaccatt atggcagcat tcactgggaa | 1320 |
| tacagagggg agaacatctg acatgagaac cgaaatcata aggctgatgg aaagtgcaag | 1380 |
| accagaagat gtgtctttcc aggggcgggg agtcttcgag ctctcggacg aaaaggcaac | 1440 |
| gagcccgatc gtgccctcct ttgacatgag taatgaagga tcttatttct tcggagacaa | 1500 |
| tgcagaggag tacgacaatt aaagaa | 1526 |

<210> SEQ ID NO 8
<211> LENGTH: 1368
<212> TYPE: DNA
<213> ORGANISM: Artificial Sequence
<220> FEATURE:
<223> OTHER INFORMATION: plasmid pHH21-NA

<400> SEQUENCE: 8

| | |
|---|---:|
| atgaatccaa accagaaaat aataaccatt gggtcaatct gtatggtagt cggaataatt | 60 |
| agcctaatat tgcaaatagg aaatataatc tcaatatgga ttagccattc aattcaaacc | 120 |
| ggaaatcaaa accatactgg aatatgcaac caaggcagca ttacctataa agttgttgct | 180 |
| gggcaggact caacttcagt gatattaacc ggcaattcat ctctttgtcc catccgtggg | 240 |
| tgggctatac acagcaaaga caatggcata agaattggtt ccaaggaga cgttttgtc | 300 |
| ataagagagc ttttatttc atgttctcac ttggaatgca ggacctttt tctgactcaa | 360 |
| ggcgccttac tgaatgacaa gcattcaagg gggacctta aggacagaag ccccttatagg | 420 |
| gccttaatga gctgccctgt cggtgaagct ccgtccccgt acaattcaag gtttgaatcg | 480 |

| | |
|---|---|
| gttgcttggt cagcaagtgc atgtcatgat ggaatgggct ggctaacaat cggaatttct | 540 |
| ggtccagatg atggagcagt ggctgtatta aaatacaacg gcataataac tgaaaccata | 600 |
| aaaagttgga ggaagaatat attgagaaca caagagtctg aatgtacctg tgtaaatggt | 660 |
| tcatgtttta ccataatgac cgatggccca agtgatgggc tggcctcgta caaaattttc | 720 |
| aagatcgaga aggggaaggt tactaaatca atagagttga atgcacctaa ttctcactac | 780 |
| gaggaatgtt cctgttaccc tgataccggc aaagtgatgt gtgtgtgcag agacaattgg | 840 |
| cacggttcga accgaccatg ggtgtccttc gaccaaaacc tagattataa aataggatac | 900 |
| atctgcagtg gggttttcgg tgacaacccg cgtcccaaag atggaacagg cagctgtggc | 960 |
| ccagtgtctg ctgatggagc aaacggagta aagggatttt catataagta tggtaatggt | 1020 |
| gtttggatag gaaggactaa aagtgacagt tccagacatg gtttgagat gatttgggat | 1080 |
| cctaatggat ggacagagac tgatagtagg ttctctatga caagatgt tgtggcaatg | 1140 |
| actgatcggt cagggtacag cggaagtttc gttcaacatc ctgagctaac agggctagac | 1200 |
| tgtatgaggc cttgcttctg ggttgaatta atcaggggc tacctgagga aacgcaatc | 1260 |
| tggactagtg ggagcatcat ttcttttgt ggtgtgaata gtgatactgt agattggtct | 1320 |
| tggccagacg tgctgagtt gccgttcacc attgacaagt agtttgtt | 1368 |

<210> SEQ ID NO 9
<211> LENGTH: 845
<212> TYPE: DNA
<213> ORGANISM: Artificial Sequence
<220> FEATURE:
<223> OTHER INFORMATION: plasmid pHH21-NS

<400> SEQUENCE: 9

| | |
|---|---|
| aatggatcca acactgtgt caagctttca ggtagattgc tttctttggc atgtccgcaa | 60 |
| aagagttgca gaccaagaac taggtgatgc cccattcctt gatcggcttc gccgagatca | 120 |
| gaagtcccta gaggaagag gcagcactct cggtctggac atcgaaacag ccacccgtgc | 180 |
| tggaaagcaa atagtggagc ggattctgaa ggaagaatct gatgaggcac tcaaaatgac | 240 |
| catggcctct gtacctgcat cgcgctacct aactgacatg actcttgagg aaatgtcaag | 300 |
| gcactggttc atgctcatgc ccaagcagaa agtggcaggc cctctttgta tcagaatgga | 360 |
| ccaggcgatc atggataaga acatcatact gaaagcgaac ttcagtgtga ttttttgaccg | 420 |
| gctggagact ctaatattac taagggcctt caccgaagag gggacaattg ttggcgaaat | 480 |
| ttcaccactg ccctctcttc caggacatac tgatgaggat gtcaaaaatg cagttgggt | 540 |
| cctcatcgga ggacttgaat ggaataataa cacagttcga gtctctgaaa ctctacagag | 600 |
| attcgcttgg agaagcagta atgagaatgg gagacctcca ctcactccaa aacagaaacg | 660 |
| gaaaatggcg ggaacaatta ggtcagaagt ttgaagaaat aagatggttg attgaagaag | 720 |
| tgagacacag actgaagata acagagaata gtttttgagca ataacatttt atgcaagcct | 780 |
| tacaactatt gcttgaagtg gagcaagaga taagaacttt ctcgtttcag cttatttaat | 840 |
| aataa | 845 |

<210> SEQ ID NO 10
<211> LENGTH: 1526
<212> TYPE: DNA
<213> ORGANISM: Artificial Sequence
<220> FEATURE:
<223> OTHER INFORMATION: Recombinant coding region

<400> SEQUENCE: 10

```
tcactcacag agtgacatcg aaatcatggc gaccaaaggc accaaacgat cttacgaaca      60
gatggagact gatggagaac gccagaatgc cactgaaatc agagcatctg tcggaaaaat     120
gattgatgga attggacgat tctacatcca aatgtgcacc gaacttaaac tcagtgatta     180
tgagggacgg ctgattcaga acagcttaac aatagagaga atggtgctct ctgcttttga     240
cgagaggagg aataaatatc tagaagaaca tcccagtgcg gggaaagatc taagaaaac      300
tggaggacct atatacagga gagtagatgg aaagtggagg agagaactca tcctttatga     360
caaagaagaa ataagacgaa tctggcgcca agctaataat ggtgacgatg caacggctgg     420
tctgactcac atgatgatct ggcactccaa tttgaatgat gcaacttacc agaggacaag     480
agctcttgtt cgcacaggaa tggatcccag gatgtgctca ctgatgcagg gttcaaccct     540
ccctaggagg tctggggccg caggtgctgc agtcaaagga gttggaacaa tggtgatgga     600
attgatcaga atgatcaaac gtgggatcaa tgatcggaac ttctggaggg gtgagaatgg     660
acggagaaca aggattgctt atgaaagaat gtgcaacatt ctcaaaggga aatttcaaac     720
agctgcacaa agaacaatgg tggatcaagt gagagagagc cggaatccag gaaatgctga     780
gttcgaagat ctcatctttt tagcacggtc tgcactcata ttgagagggt cagttgctca     840
caagtcctgc ctgcctgcct gtgtgtatgg atctgccgta gccagtggat acgactttga     900
aagagaggga tactctctag tcggaataga ccctttcaga ctgcttcaaa acagccaagt     960
atacagccta atcagaccaa atgagaatcc agcacacaag agtcaactgg tgtggatggc    1020
atgccattct gctgcatttg aagatctaag agtatcaagc ttcatcagag ggacgaaagt    1080
ggtcccaaga gggaagcttt ccactagagg agttcaaatt gcttccaatg aaaacatgga    1140
gactatggaa tcaagtaccc ttgaactgag aagcagattc tgggccataa ggaccagaag    1200
tggagggaac accaatcaac agagggcttc ctcgggccaa atcagcatac aacctacgtt    1260
ctcagtacag agaaatctcc cttttgacag accaaccatt atggcagcat tcactgggaa    1320
tacagagggg agaacatctg acatgagaac cgaaatcata aggctgatgg aaagtgcaag    1380
accagaagat gtgtctttcc aggggcgggg agtcttcgag ctctcggacg aaaaggcaac    1440
gagcccgatc gtgccctcct tgacatgag taatgaagga tcttatttct tcggagacaa    1500
tgcagaggag tacgacaatt aaagaa                                         1526
```

<210> SEQ ID NO 11
<211> LENGTH: 40
<212> TYPE: DNA
<213> ORGANISM: Artificial Sequence
<220> FEATURE:
<223> OTHER INFORMATION: primer

<400> SEQUENCE: 11

```
ctgagaagca gagcgtgggc cataaggacc agaagtggag                            40
```

<210> SEQ ID NO 12
<211> LENGTH: 41
<212> TYPE: DNA
<213> ORGANISM: Artificial Sequence
<220> FEATURE:
<223> OTHER INFORMATION: primer

<400> SEQUENCE: 12

```
ccttatggcc cacgctctgc ttctcagttc aagggtactt g                          41
```

<210> SEQ ID NO 13

```
<211> LENGTH: 40
<212> TYPE: DNA
<213> ORGANISM: Artificial Sequence
<220> FEATURE:
<223> OTHER INFORMATION: primer

<400> SEQUENCE: 13
ctgagaagca gattctgggc cataaggacc agaagtggag                              40

<210> SEQ ID NO 14
<211> LENGTH: 41
<212> TYPE: DNA
<213> ORGANISM: Artificial Sequence
<220> FEATURE:
<223> OTHER INFORMATION: primer

<400> SEQUENCE: 14
ccttatggcc cagaatctgc ttctcagttc aagggtactt g                            41

<210> SEQ ID NO 15
<211> LENGTH: 40
<212> TYPE: DNA
<213> ORGANISM: Artificial Sequence
<220> FEATURE:
<223> OTHER INFORMATION: primer

<400> SEQUENCE: 15
ctgagaagca gagagtgggc cataaggacc agaagtggag                              40

<210> SEQ ID NO 16
<211> LENGTH: 41
<212> TYPE: DNA
<213> ORGANISM: Artificial Sequence
<220> FEATURE:
<223> OTHER INFORMATION: primer

<400> SEQUENCE: 16
ccttatggcc cactctctgc ttctcagttc aagggtactt g                            41
```

US 10,538,745 B2

KEY PHOSPHORYLATION SITE OF TEMPERATURE SENSITIVITY OF INFLUENZA A VIRUS AND USE THEREOF

TECHNICAL FIELD

The present invention relates to a key phosphorylation site of temperature sensitivity of influenza A virus and use thereof.

BACKGROUND

Influenza A virus comprises eight segmented RNA fragments, and 14 viral proteins can be encoded by utilizing the RNA fragments. The completion of replication and transcription of the viral genome need a functional unit, RNP complex. Virus, when infecting host cells, is faced with 2 barriers and 4 shuttles.

The first barrier is cytoplasmic membrane, which is passed through by the virus when it enters a cell, at this time the virus binds to a sialic acid receptor on the surface of the cell using hemagglutinin protein HA, and invades into the inside of the host cell via endocytosis.

Matrix protein M1 then releases vRNP complex into the cytoplasm, since genomic replication and transcription need to occur in the nucleus, at this time, the vRNP complex is faced with the second barrier, the nuclear membrane. VRNP binds to the nuclear transport receptor protein importin-α using atypical bidirectional NLS at N-terminal of the NP protein, so as to pass through the nuclear pore complex and enter the inside of the nucleus to initiate replication and transcription.

The mRNA generated by transcription is translated in the cytoplasm, and the newly synthesized viral polymerase components, in turn, use their own NLS to enter the nucleus, respectively and reassemble into RNP complex.

After replication of the viral genome is completed, the RNP complex will utilize the NP protein, together with the M1 protein and the NEP protein, to form a large complex, which is transported to the cytoplasm by the cytoplasmic transport protein CRM1 protein, such that another barrier shuttle is completed, and then complete virus particles are assembled.

The NP protein plays an important role in the process of two nuclear membranes shuttles.

DISCLOSURE OF THE INVENTION

An object of the present invention is to provide a key phosphorylation site of temperature sensitivity of influenza A virus and use thereof.

The present invention firstly protects a recombinant virus named as WSN-Y385F, which is a recombinant virus obtained by mutating a codon that encodes tyrosine residue at position 385 of NP protein in the genome of influenza A virus to a codon of phenylalanine residue. The virus WSN-Y385F is a temperature-sensitive virus that can normally replicate and survive at 37° C., but cannot normally replicate and cannot survive at 33° C.

The influenza A virus may specifically be WSN virus A/WSN/1933 (H1N1) strain.

The NP protein is as shown in SEQ ID NO: 1 of the Sequence Listing.

The present invention further protects a protein named as NP-Y385F, which is a protein obtained by mutating a tyrosine residue at position 385 of NP protein to a phenylalanine residue.

The NP protein is as shown in SEQ ID NO: 1 of the Sequence Listing.

A gene encoding protein NP-Y385F also belongs to the protection scope of the present invention. The gene encoding the protein NP-Y385F is named as gene NP-Y385F.

The gene NP-Y385F can specifically be (a) or (b) as follows:

(a) a DNA molecule whose coding region is as shown in nucleotides at the position of 26-1522 from 5' end of SEQ ID NO: 10 in the Sequence Listing;

(b) a DNA molecule shown in SEQ ID NO: 10 in the Sequence Listing.

A recombinant plasmid comprising the gene NP-Y385F also belongs to the protection scope of the present invention.

The recombinant plasmid comprising the gene NP-Y385F may specifically be recombinant plasmid pHH21-NP-Y385F. The recombinant plasmid pHH21-NP-Y385F is a recombinant plasmid obtained by inserting the gene NP-Y385F at the multiple cloning site (for example, a BsmBI restriction site) of a vector pHH21.

The recombinant plasmid comprising the gene NP-Y385F may specifically be a recombinant plasmid pcDNA3.0-NP-Y385F. The recombinant plasmid pcDNA3.0-NP-Y385F is a recombinant plasmid obtained by inserting the gene NP-Y385F at the multiple cloning site (for example, between KpnI and XhoI restriction sites) of a vector pcDNA3.0.

The present invention further protects a temperature-sensitive recombinant virus, and a preparation method thereof comprises the following steps:

The plasmid pHH21-PA, plasmid pHH21-PB1, plasmid pHH21-PB2, plasmid pHH21-HA, plasmid pHH21-NA, plasmid pHH21-M, plasmid pHH21-NS, plasmid pcDNA3.0-PA, plasmid pcDNA3.0-PB1, plasmid pcDNA3.0-PB2, recombinant plasmid pHH21-NP-Y385F and recombinant plasmid pcDNA3.0-NP-Y385F are co-transfected into in vitro mammalian cells, then the cells are cultured to obtain the recombinant virus;

The plasmid pHH21-PA is a plasmid obtained by inserting a double-stranded DNA molecule shown as SEQ ID NO: 3 in the Sequence Listing into the multiple cloning site of a vector pHH21 (for example, a BsmBI restriction site); the plasmid pHH21-PB1 is a plasmid obtained by inserting a double-stranded DNA molecule shown as SEQ ID NO: 4 in the Sequence Listing into the multiple cloning site of a vector pHH21 (for example, a BsmBI restriction site); the plasmid pHH21-PB2 can specifically be a plasmid obtained by inserting a double-stranded DNA molecule shown as SEQ ID NO: 5 in the Sequence Listing into the multiple cloning site of a vector pHH21 (for example, a BsmBI restriction site); the plasmid pHH21-HA is a plasmid obtained by inserting a double-stranded DNA molecule shown as SEQ ID NO: 6 in the Sequence Listing into the multiple cloning site of a vector pHH21 (for example, a BsmBI restriction site); the plasmid pHH21-NA is a plasmid obtained by inserting a double-stranded DNA molecule shown as SEQ ID NO: 8 in the Sequence Listing into the multiple cloning site of a vector pHH21 (for example, a BsmBI restriction site); the plasmid pHH21-M is a plasmid obtained by inserting a double-stranded DNA molecule shown as SEQ ID NO: 2 in the Sequence Listing into the multiple cloning site of a vector pHH21 (for example, a BsmBI restriction site); the plasmid pHH21-NS is a plasmid obtained by inserting a double-stranded DNA molecule shown as SEQ ID NO: 9 in the Sequence Listing into the multiple cloning site of a vector pHH21 (for example, a BsmBI restriction site); the plasmid pcDNA3.0-PA is a plasmid obtained by inserting a double-stranded DNA molecule shown as SEQ ID NO: 3 in the Sequence Listing into the multiple cloning site of a vector pcDNA3.0 (for example, between KpnI and XhoI restriction sites); the plasmid pcDNA3.0-PB1 is a plasmid obtained by inserting a double-stranded DNA molecule shown as SEQ ID NO: 4 in the Sequence Listing into the multiple cloning site of a vector pcDNA3.0 (for example, between KpnI and XhoI restriction sites); the plasmid pcDNA3.0-PB2 is a plasmid obtained by inserting a double-stranded DNA molecule shown as SEQ ID NO: 5 in the Sequence Listing into the multiple cloning site of the vector pcDNA3.0 (for example, between KpnI and XhoI restriction sites); the recombinant plasmid pHH21-NP-Y385F is a plasmid obtained by inserting the gene NP-Y385F at the multiple cloning site of a vector pHH21 (for example, a BsmBI restriction site); and the recombinant plasmid pcDNA3.0-NP-Y385F is a plasmid obtained by inserting the gene NP-Y385F at the multiple cloning site of a vector pcDNA3.0 (for example, between KpnI and XhoI restriction sites).

The mammalian cells may specifically be HEK 293T/17 cells.

The culture condition may specifically be culturing at 37° C. for 6 to 78 hours.

The present invention further protects a method for inhibiting phosphorylation of a NP protein of influenza A virus by mutating an amino acid residue at position 385 from N terminal of the NP protein of the influenza A virus from a tyrosine to a phenylalanine. The present invention further protects a method for reducing phosphorylation level of a NP protein of influenza A virus by mutating an amino acid residue at position 385 from N terminal of the NP protein of the influenza A virus from a tyrosine to a phenylalanine. The present invention further protects a method for inhibiting phosphorylation of a NP protein of influenza A virus by mutating a codon encoding an amino acid residue at position 385 from N terminal of the NP protein in the genome of influenza A virus from a tyrosine codon to a phenylalanine codon.

The present invention further protects a method for reducing phosphorylation level of a NP protein of influenza A virus by mutating a codon encoding an amino acid residue at position 385 from N terminal of the NP protein in the genome of influenza A virus from a tyrosine codon to a phenylalanine codon.

The NP protein is shown in SEQ ID NO: 1 of the Sequence Listing.

The present invention further protects use of any one of the above recombinant viruses in the preparation of influenza A virus vaccine.

The present invention further protects use of any one of the above recombinant viruses as influenza A virus vaccine.

The present invention further protects an influenza A virus vaccine whose active ingredient is any one of the above recombinant viruses.

The present invention further protects a plasmid combination consisting of plasmid pHH21-PA, plasmid pHH21-PB1, plasmid pHH21-PB2, plasmid pHH21-HA, plasmid pHH21-NA, plasmid pHH21-M, plasmid pHH21-NS, plasmid pcDNA3.0-PA, plasmid pcDNA3.0-PB1, plasmid pcDNA3.0-PB2, recombinant plasmid pHH21-NP-Y385F and recombinant plasmid pcDNA3.0-NP-Y385F. Each plasmid can be separately packaged, and all the plasmids can also be mixed and packaged, and any several plasmids in the combination can also be mixed and packaged.

The invention further protects a kit for preparing the recombinant virus (virus WSN-Y385F), the kit comprises the plasmid combination. The kit can further comprise an isolated mammal cell. The mammalian cells can specifically be HEK293T 17 cells.

Any one of the above influenza A virus may specifically be a WSN virus A/WSN/1933 (H1N1) strain.

THE BEST MODE FOR CARRYING OUT THE INVENTION

Figure 1:
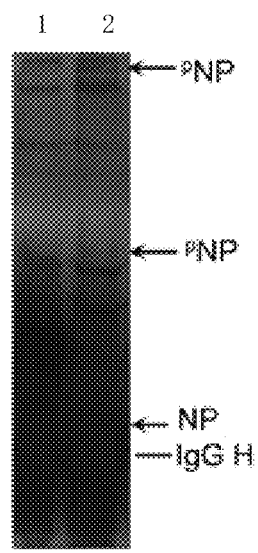
FIG. 1 shows the result of step 1 of Example 1.

The following Examples will provide a better understanding of the present invention, but do not limit the invention. The experimental methods in the following Examples, unless otherwise specified, are conventional methods. The test materials used in the following Examples, unless otherwise specified, all are purchased from conventional biochemical reagents stores. Quantitative tests in the following Examples are set three times to repeat the experiments and the result is the average.

WSN virus A/WSN/1933 (H1N1) strain: Neumann, G. et al., Generation of influenza A viruses entirely from cloned cDNAs. *P Natl Acad Sci Usa* 96 (16), 9345 (1999). WSN virus is the influenza virus. In the Examples, the virus infection solution is used to adjust the virus concentration so as to achieve different doses of infection.

Vector pHH21: Neumann, G. et al., Generation of influenza A viruses entirely from cloned cDNAs. *P Natl Acad Sci Usa* 96 (16), 9345 (1999).

HEK 293T/17 cells (abbreviated as 293T cell-derived line, human embryonic kidney cells): ATCC, CRL-11268. Vector pcDNA3.0: Shanghai CPG Biotech. Co., Ltd., catalog number CPC030. *E. coli* DH5α: Shanghai Beinuo Biotech. Co., Ltd. A549 cells (human lung adenocarcinoma cells): Shanghai Bioleaf Biotech Co., Ltd. BALB/c mice: Beijing Vital River Laboratory Animal Technology Co., Ltd. MDCK cells: ATCC, CCL-34.

Cell lysis solution (pH 7.4): comprising 150 mM sodium chloride, 20 mM HEPES, 10% (by volume) glycerol, 1 mM EDTA, 1 g/100 mL NP40, protease inhibitor (cocktail), and the balance water.

Elution buffer: the concentration of sodium chloride is 300 mM, the other components are same as those in the cell lysis solution.

Virus infection solution: comprising 2 µg/ml TPCK-treated trypsin (trypsin is added in a manner of trypsin stock solution, and the trypsin stock solution is a solution with the trypsin concentration of 0.25 g/100 mL formulated in PBS buffer), 100 U/ml penicillin and 100 U/ml streptomycin in serum-free DMEM medium.

Alkaline phosphatase: Takara, catalog number D2250. Protease inhibitor (cocktail) is purchased from Roche company. SDM enzyme: Beijing SBS Genetech Co., Ltd., catalog number: SDM-15. The gel used in phos-tag SDS-PAGE is Phos-tag Acrylamide that is purchased from Wako (Japan). Anti-phosphotyrosine antibody (murine monoclonal antibody, sc-508) is purchased from Santa Cruz. Pre-stained protein standard with known molecular weight is purchased from Thermo. Sodium chloride, N-(2-hydroxyethyl) piperazine-N'-2-ethanesulfonic acid (abbreviated as HEPES), glycerin, ethylenediaminetetraacetic acid (abbreviated as EDTA), Nonidet P-40 (abbreviated as NP 40) and TPCK-treated trypsin are all purchased from Sigma. Bovine serum albumin (BSA) is purchased from Jiang Chen Bio. Penicillin and streptomycin are purchased from Beyotime company. Sodium dodecyl sulfate (abbreviated as SDS) and low melting point agarose are purchased from Amersco Company.

Anti-NP protein monoclonal antibody (i.e. murine monoclonal antibody against influenza A virus NP protein): M-R Yu#, X-L Liu#, Sh Cao, Zh-D Zhao, K Zhang, Q Xie, C-W Chen, Sh-Y Gao, Y-H Bi, L Sun, X Ye, George F. Gao, W-J Liu*. 2012. Identification and Characterization of three novel nuclear export signals in influenza A virus nucleoprotein. Journal of Virology, 86(9):4970-80.

Plasmid pHH21-PA, plasmid pHH21-PB1, plasmid pHH21-PB2, plasmid pHH21-HA, plasmid pHH21-NP, plasmid pHH21-NA, plasmid pHH21-M, plasmid pHH21-NS, plasmid pcDNA3.0-PA, plasmid pcDNA3.0-PB1, plasmid pcDNA3.0-PB2 and plasmid pcDNA3.0-NP are co-transfected into HEK 293T/17 cells, then the cells are cultured to obtain WSN virus A/WSN/1933 (H1N1) strain. WSN virus A/WSN/1933 (H1N1) strain is also known as WSN virus wild type.

Example 1. Obtainment of Phosphorylated NP Protein and Identification of Phosphorylation Sites I. Obtainment of Phosphorylated NP Protein 1. HEK 293T/17 cells were infected with A/WSN/1933 (H1N1) strain at a dose of MOI=0.1 and harvested after being cultured at 37° C. for 12-16 hours.

2. The cells harvested in step 1 were treated with cell lysis solution at 4° C. for 30 minutes and centrifuged at 12000 rpm for 15 minutes, the supernatant was collected.

3. Anti-NP protein monoclonal antibody was added to the supernatant obtained in step 2 and incubated at 4° C. for 1 hour. Then protein G beads were added and incubated at 4° C. for 3 hours. The supernatant was discarded, and the beads were washed with elution buffer 3 times (10 minutes each time) at 4° C., the substance bound to the beads was the NP protein.

4. The NP protein-bound beads obtained in step 3 were treated with alkaline phosphatase at 37° C. for 2 hours (the function of the alkaline phosphatase was to dephosphorylate the phosphorylated protein).

5. The NP protein prior to alkaline phosphatase treatment (obtained in Step 3) and the NP protein after alkaline phosphatase treatment (obtained in Step 4) were respectively subjected to phos-tag SDS-PAGE and silver staining for coloration.

The result was shown in FIG. 1. In FIG. 1, lane 1 was the NP protein after alkaline phosphatase treatment and lane 2 was the NP protein prior to alkaline phosphatase treatment. The NP protein after alkaline phosphatase treatment was used as a standard NP protein, a band in which the NP protein prior to alkaline phosphatase treatment on the gel presents slower migration rate than that of the standard NP protein and sensitive to alkaline phosphatase was the phosphorylated NP band. The results showed that the NP protein obtained in step 3 was a phosphorylated protein that can be dephosphorylated by alkaline phosphatase.

II. Phosphorylation Sites were Identified by Mass Spectrometry

The phosphorylated NP band was cut from the gel and sent to a large instrument platform of the Institute of Zoology, Chinese Academy of Sciences, for sample processing and mass spectrometry identification (Nano-LC MS/MS, LCQ DECA XP$^{PLUS}$ Thermo).

Figure 2:
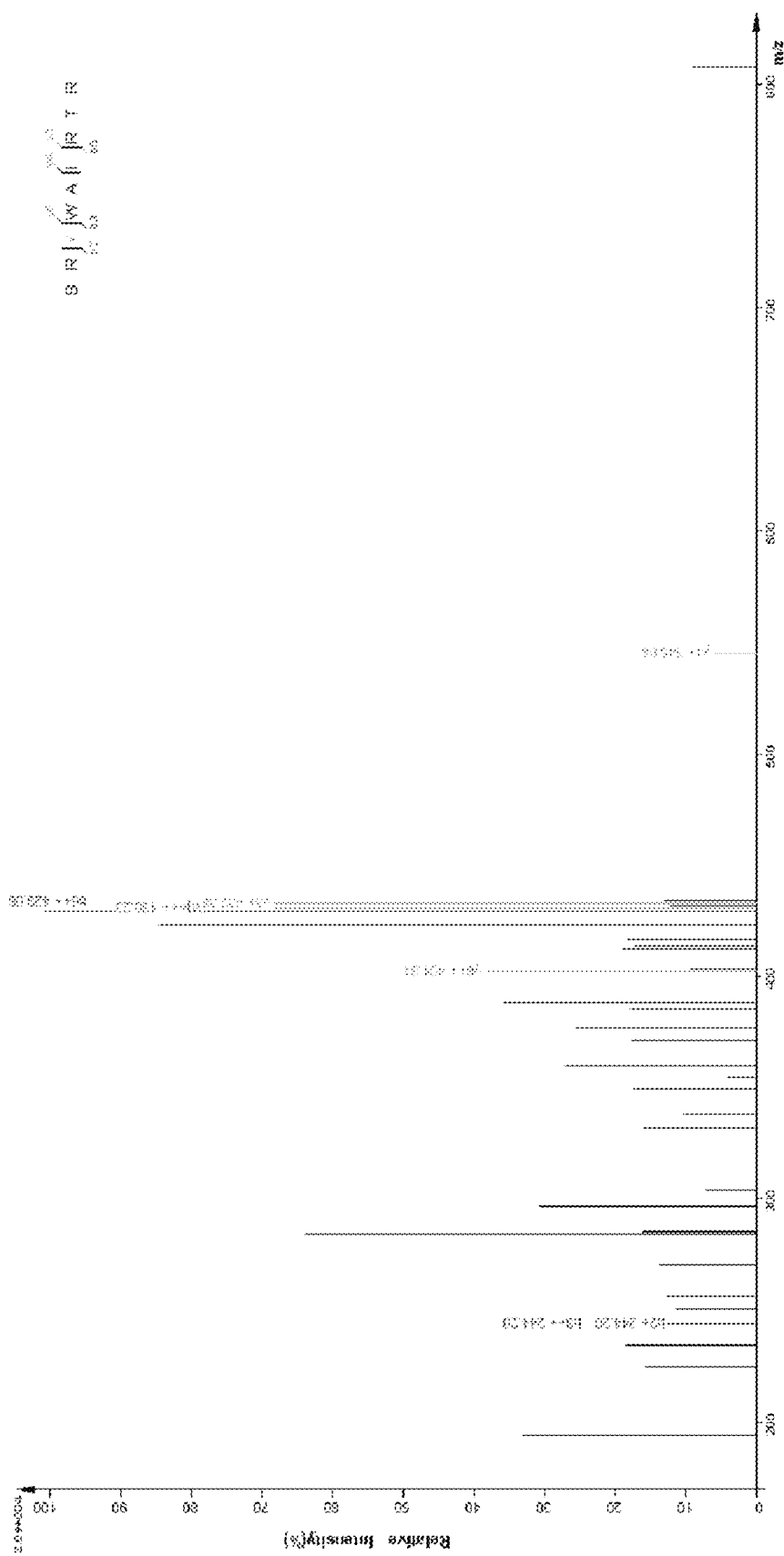
FIG. 2 shows the result of step 2 of Example 1.

The result was shown in FIG. 2. The difference in nuclear mass ratio between B2 and b3 indicated that Y385 was modified by phosphorylation. The identification result showed that the band was the NP protein of influenza A virus and there was a phosphorylation modification at tyrosine residue at position 385.

Example 2. Preparation and Phosphorylation Identification of the Mutant Protein

I. Construction of Recombinant Plasmids

1. Construction of Plasmid pHH21-PA

The double stranded DNA molecule shown in SEQ ID NO: 3 of the Sequence Listing was inserted into the BsmBI restriction site of vector pHH21 to obtain a plasmid pHH21-PA.

2. Construction of Plasmid pHH21-PB1

The double stranded DNA molecule shown in SEQ ID NO: 4 of the Sequence Listing was inserted into the BsmBI restriction site of vector pHH21 to obtain a plasmid pHH21-PB1.

3. Construction of Plasmid pHH21-PB2

The double-stranded DNA molecule shown in SEQ ID NO: 5 of the Sequence Listing was inserted into the BsmBI restriction site of vector pHH21 to obtain a plasmid pHH21-PB2.

4. Construction of Plasmid pHH21-HA

The double stranded DNA molecule shown in SEQ ID NO: 6 of the Sequence Listing was inserted into the BsmBI restriction site of vector pHH21 to obtain a plasmid pHH21-HA.

5. Construction of Plasmid pHH21-NP

The double stranded DNA molecule shown in SEQ ID NO: 7 of the Sequence Listing was inserted into the BsmBI restriction site of vector pHH21 to obtain a plasmid pHH21-NP.

6. Construction of Plasmid pHH21-NA

The double stranded DNA molecule shown in SEQ ID NO: 8 of the Sequence Listing was inserted into the BsmBI restriction site of vector pHH21 to obtain a plasmid pHH21-NA.

7. Construction of Plasmid pHH21-M

The double stranded DNA molecule shown in SEQ ID NO: 2 of the Sequence Listing was inserted into the BsmBI restriction site of vector pHH21 to obtain a plasmid pHH21-M.

8. Construction of Plasmid pHH21-NS

The double stranded DNA molecule shown in SEQ ID NO: 9 of the Sequence Listing was inserted into the BsmBI restriction site of vector pHH21 to obtain a plasmid pHH21-NS.

9. Construction of Plasmid pcDNA3.0-PA

The double-stranded DNA molecule shown in SEQ ID NO: 3 of the Sequence Listing was inserted between the KpnI and XhoI restriction sites of vector pcDNA 3.0 to obtain a plasmid pcDNA3.0-PA.

10. Construction of Plasmid pcDNA3.0-PB1

The double stranded DNA molecule shown in SEQ ID NO: 4 of the Sequence Listing was inserted between the KpnI and XhoI restriction sites of vector pcDNA3.0 to obtain a plasmid pcDNA3.0-PB1.

11. Construction of Plasmid pcDNA3.0-PB2

The double stranded DNA molecule shown in SEQ ID NO: 5 of the Sequence Listing was inserted between the KpnI and XhoI restriction sites of vector pcDNA3.0 to obtain a plasmid pcDNA3.0-PB2.

12. Construction of Plasmid pcDNA3.0-NP

The double stranded DNA molecule shown in SEQ ID NO: 7 of the Sequence Listing was inserted between the KpnI and XhoI restriction sites of vector pcDNA3.0 to obtain a plasmid pcDNA3.0-NP.

13. Construction of Recombinant Plasmids

NP-Y385A-F: 5'-ctgagaagcagaGCGtgggccataaggaccagaagtggag-3' (SEQ ID NO: 11);
NP-Y385A-R: 5'-ccttatggcccaCGCtctgcttctcagttcaagggtacttg-3' (SEQ ID NO: 12).
NP-Y385F-F: 5'-ctgagaagcagaTTCtgggccataaggaccagaagtggag-3' (SEQ ID NO: 13);
NP-Y385F-R: 5'-ccttatggcccaGAAtctgcttctcagttcaagggtacttg-3', (SEQ ID NO: 14).
NP-Y385E-F: 5'-ctgagaagcagaGAGtgggccataaggaccagaagtggag-3', (SEQ ID NO: 15);
NP-Y385E-R: 5'-ccttatggcccaCTCtctgcttctcagttcaagggtacttg-3', SEQ ID NO: 16).

A variety of recombinant plasmids were constructed using Newpep point mutation kit (Cat. No. 80111-01, Beijing Newpep Biolotechn Co., Ltd.) according to the kit instructions.

(1) PCR amplification was carried out using the plasmid pHH21-NP as a template, and a primer pair consisting of NP-Y385A-F and NP-Y385A-R to obtain a PCR amplification product (mutating a plasmid).

(2) The PCR amplification product in step (1) was digested with SDM enzyme at 37° C. for 2 hours (digesting a template plasmid).

(3) The product in step (2) was transformed into competent cells of E. coli DH5α to obtain a recombinant bacterium Y385A-I (i.e. E. coli comprising the recombinant plasmid pHH21-NP-Y385A). Based on the sequencing results, the recombinant plasmid pHH21-NP-Y385A was structurally described as follows: codon "tac" encoding tyrosine at position 385 from N-terminal of the NP protein in the plasmid pHH21-NP was mutated to codon "GCG" of alanine.

(4) PCR amplification was carried out using pcDNA3.0-NP as a template, and a primer pair consisting of NP-Y385A-F and NP-Y385A-R to obtain a PCR amplification product (mutating a plasmid).

(5) The PCR amplification product in step (4) was digested with SDM enzyme at 37° C. for 2 hours (digesting a template plasmid).

(6) The product in step (5) was transformed into competent cells of E. coli DH5α to obtain a recombinant bacterium Y385A-II (i.e. E. coli comprising the recombinant plasmid pcDNA3.0-NP-Y385A). Based on the sequencing results, the recombinant plasmid pcDNA3.0-NP-Y385A was structurally described as follows: codon "tac" encoding tyrosine at position 385 from N-terminal of the NP protein in the plasmid pcDNA3.0-NP was mutated to codon "GCG" of alanine.

(7) PCR amplification was carried out using the plasmid pHH21-NP as a template, and a primer pair consisting of NP-Y385F-F and NP-Y385F-R to obtain a PCR amplification product (mutating a plasmid).

(8) The PCR amplification product in step (7) was digested with SDM enzyme at 37° C. for 2 hours (digesting a template plasmid).

(9) The product in step (8) was transformed into competent cells of E. coli DH5α to obtain a recombinant bacterium Y385F-I (i.e. E. coli comprising the recombinant plasmid pHH21-NP-Y385F). Based on the sequencing results, the recombinant plasmid pHH21-NP-Y385F was structurally described as follows: codon "tac" encoding tyrosine at position 385 from N-terminal of the NP protein in the plasmid pHH21-NP was mutated to codon "TTC" of phenylalanine; that was, the double stranded DNA molecule shown in SEQ ID NO: 10 of the Sequence Listing was inserted into the BsmBI restriction site of the vector pHH21.

(10) PCR amplification was carried out using pcDNA3.0-NP as a template, and a primer pair consisting of NP-Y385F-F and NP-Y385F-R to obtain a PCR amplification product (mutating plasmid).

(11) The PCR amplification product in step (10) was digested with SDM enzyme at 37° C. for 2 hours (digesting a template plasmid).

(12) The product in step (11) was transformed into competent cells of E. coli DH5α to obtain a recombinant bacterium Y385F-II (i.e. E. coli comprising the recombinant plasmid pcDNA3.0-NP-Y385F). Based on the sequencing results, the recombinant plasmid pcDNA3.0-NP-Y385F was structurally described as follows: codon "tac" encoding tyrosine at position 385 from N-terminal of the NP protein in the plasmid pcDNA3.0-NP was mutated to codon "TTC" of phenylalanine; that was, the double stranded DNA molecule shown in SEQ ID NO: 10 of the Sequence Listing was inserted between the KpnI and XhoI restriction sites of the vector pcDNA3.0.

(13) PCR amplification was carried out using the plasmid pHH21-NP as a template, and a primer pair consisting of NP-Y385E-F and NP-Y385E-R to obtain a PCR amplification product (mutating a plasmid).

(14) The PCR amplification product in step (13) was digested with SDM enzyme at 37° C. for 2 hours (digesting a template plasmid).

(15) The product in step (14) was transformed into competent cells of E. coli DH5a to obtain a recombinant bacterium Y385E-I (i.e. E. coli comprising the recombinant plasmid pHH21-NP-Y385E). Based on the sequencing results, the recombinant plasmid pHH21-NP-Y385E was structurally described as follows: codon "tac" encoding tyrosine at position 385 from N-terminal of the NP protein in the plasmid pHH21-NP was mutated to codon "GAG" of glutamic acid.

(16) PCR amplification was carried out using the plasmid pcDNA3.0-NP as a template, and a primer pair consisting of NP-Y385E-F and NP-Y385E-R to obtain a PCR amplification product (mutating a plasmid).

(17) The PCR amplification product in step (16) was digested with SDM enzyme at 37° C. for 2 hours (digesting a template plasmid).

(18) The product in step (17) was transformed into competent cells of E. coli DH5a to obtain a recombinant bacterium Y385E-II (i.e. E. coli comprising the recombinant plasmid pcDNA3.0-NP-Y385E). Based on the sequencing results, the recombinant plasmid pcDNA3.0-NP-Y385E was structurally described as follows: codon "tac" encoding tyrosine at position 385 from N-terminal of the NP protein in the plasmid pcDNA3.0-NP was mutated to codon "GAG" of glutamic acid.

II. Preparation of the Mutant Proteins

1. Preparation of Y385F Mutant Protein (1) Plasmid pHH21-PA, plasmid pHH21-PB1, plasmid pHH21-PB2, plasmid pHH21-HA, recombinant plasmid pHH21-NP-Y385F, plasmid pHH21-NA, plasmid pHH21-M, plasmid pHH21-NS, plasmid pcDNA3.0-PA, plasmid pcDNA3.0-PB1, plasmid pcDNA3.0-PB2 and recombinant plasmid pcDNA3.0-NP-Y385F were co-transfected into HEK 293T/17 cells by liposome Lipofectamine 2000 (Invitrogen) at a equal mass ratio, and the cells were cultured at 37° C. for 6 hours.

(2) Culture medium of cells in step (1) was replaced by virus infection solution, and the cells were harvested after 72 hours of culture at 37° C.

(3) The cells harvested in step (2) were treated with cell lysis solution at 4° C. for 30 minutes and centrifuged at 12000 rpm for 15 minutes, and the supernatant was collected.

(4) Anti-NP protein monoclonal antibody was added to the supernatant obtained in step (3), incubated at 4° C. for 1 hour. Then protein G beads were added and incubated at 4° C. for 3 hours. The supernatant was discarded, and the beads were washed with elution buffer 3 times (10 minutes each time) at 4° C., the substance bound to the beads was the NP protein.

2. Preparation of the NP Protein

Recombinant plasmid pHH21-NP-Y385F was replaced by plasmid pHH21-NP and the recombinant plasmid pcDNA3.0-NP-Y385F was replaced by plasmid pcDNA3.0-NP, and the others were the same as those in step 1, the substance bound to the beads was the NP protein.

3. Western Blot Detection

The proteins obtained in step 1 and step 2 were subjected to western blot, respectively. The primary antibody used was anti-phosphorylated tyrosine antibody, and the secondary antibody used was HRP-labeled goat anti-mouse IgG.

Figure 3:
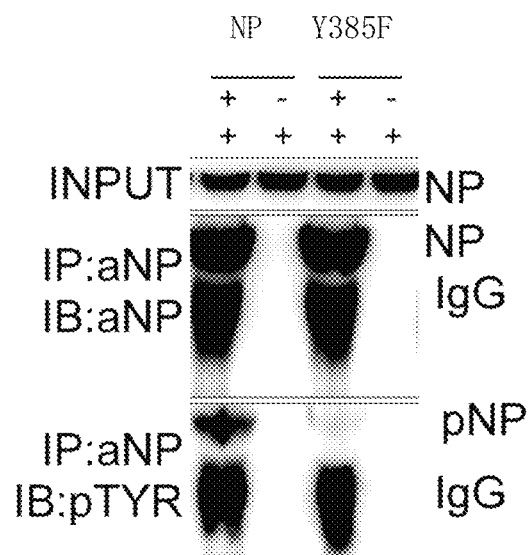
FIG. 3 shows the result of Example 2.

The result was shown in FIG. 3. The result showed that phosphorylation level of Y385F mutant protein was decreased significantly compared with a NP protein, that was, the tyrosine residue at position 385 of the NP protein was the main phosphorylation site.

Example 3. Virus Rescue

1. HEK 293T/17 cells were seeded in 60 mm dishes, $1 \times 10^6$ cells per dish, and cultured for 12 hours.

2. After step 1 was completed, HEK 293T/17 cells were grouped and treated as follows:

Group 1: plasmid pHH21-PA, plasmid pHH21-PB1, plasmid pHH21-PB2, plasmid pHH21-HA, recombinant plasmid pHH21-NP-Y385A, plasmid pHH21-NA, plasmid pHH21-M, plasmid pHH21-NS, plasmid pcDNA3.0-PA, plasmid pcDNA3.0-PB1, plasmid pcDNA3.0-PB2 and recombinant plasmid pcDNA3.0-NP-Y385A, each 0.5 μg, were co-transfected into HEK 293T/17 cells by liposome Lipofectamine 2000 (Invitrogen), after the cells were cultured at 37° C. for 6 hours, the medium was replaced by virus infection solution, and the cells were cultured for a continuation of 72 hours and were harvested.

Group 2: the difference between group 2 and group 1 only lies in that the recombinant plasmid pHH21-NP-Y385A was replaced by the recombinant plasmid pHH21-NP-Y385F and the recombinant plasmid pcDNA3.0-NP-Y385A was replaced by the recombinant plasmid pcDNA3.0-NP-Y385F.

Group 3: the difference between group 3 and group 1 only lies in that the recombinant plasmid pHH21-NP-Y385A was replaced by the recombinant plasmid pHH21-NP-Y385E and the recombinant plasmid pcDNA3.0-NP-Y385A was replaced by the recombinant plasmid pcDNA3.0-NP-Y385E.

Group 4: the difference between group 4 and group 1 only lies in that the recombinant plasmid pHH21-NP-Y385A was replaced by the plasmid pHH21-NP and the recombinant plasmid pcDNA3.0-NP-Y385A was replaced by the plasmid pcDNA3.0-NP.

3. After step 2 was completed, the culture supernatant was harvested in each group. The culture supernatant obtained in the group 4 comprised wild-type WSN virus, so the culture supernatant was named as WSN-WT virus solution.

The culture supernatant obtained in the group 1 comprised mutant WSN virus (the codon encoding tyrosine at position 385 from N-terminal of the NP protein in the mutant virus genome was mutated to codon of alanine, the mutant virus was named as WSN-Y385A virus), so the culture supernatant was named as WSN-Y385A virus solution.

The culture supernatant obtained in the group 2 comprised mutant WSN virus (the codon encoding tyrosine at position 385 from N-terminal of the NP protein in the mutant virus genome was mutated to codon of phenylalanine, the mutant virus was named as WSN-Y385F virus), so the culture supernatant was named as WSN-Y385F virus solution.

The culture supernatant obtained in the group 3 comprised mutant WSN virus (the codon encoding tyrosine at position 385 from N-terminal of the NP protein in the mutant virus genome was mutated to codon of glutamic acid, the mutant virus was named as WSN-Y385E virus), so the culture supernatant was named as WSN-Y385E virus solution.

4. Each virus solution obtained in step 3 was taken for virus titer detection by plaque identification.

Plaque identification method: (1) MDCK cells were seeded in 12-well plate, about $1 \times 10^5$ cells per well, and cultured in an incubator at 37° C., 5% $CO_2$ overnight; (2) the cell medium on the surface of the cells was washed with PBS buffer, and the virus solution to be tested was diluted serially by virus infection solution and then added to each well, three replicate wells were set for each dilution, incubated at 37° C. for 1 hour; (3) the supernatant was discarded, and the cells were washed with PBS buffer, 1 ml of mixed solution (a method for preparing the mixed solution: 1 part by volume of 3% low melting point agarose melted and cooled to about 37° C. and 1 part by volume of phenol red-free DMEM medium preheated to 37° C. were mixed with equal volume, and TPCK-treated trypsin, penicillin and streptomycin were added to the mixture to make the concentration of trypsin be 2 μg/ml, the concentration of penicillin and streptomycin each be 100 U/ml) was added to each well; (4) the 12-well plate was placed at 4° C. for more than 15 minutes, after the agar was solidified, the plate was turned over to place upside down and incubated in an incubator at 37° C., cytopathic condition was observed under a microscope, after the plate was incubated for 3 days (in actual application, 2-4 days), the 12-well plate was removed from the incubator, and the number of plaque was counted. The titer of WSN-WT virus solution was 6.512 $\log_{10}$ PFU/ml. The titer of WSN-Y385F virus solution was 7.179 $\log_{10}$ PFU/ml. The titer of WSN-Y385A virus solution was 0, that was, it could not make MDCK produce a plague. The titer of WSN-Y385E virus solution was 0, i.e., it could not make MDCK produce a plague.

5. After step 2 was completed, the cells were harvested in each group, and the cells were broken and subjected to western blot (detecting the expression of each of major viral proteins).

In Western Blot: the primary antibody for detecting the NP protein was purchased from Thermo Scientific, catalog number: PAS-32242; the primary antibody for detecting the M1 protein was the monoclonal antibody against M1 protein.

Figure 4:
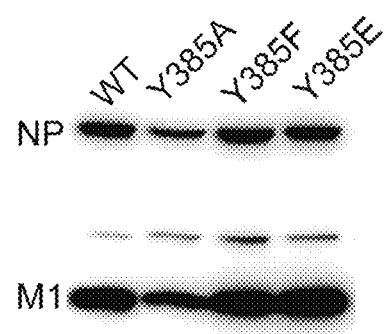
FIG. 4 shows the result of Example 3.

The result was shown in FIG. 4. Two important proteins (the NP protein and M1 protein) of influenza virus in the recombinant system in each group could be expressed normally.

Example 4. Difference in Virus Growth Curves at Different Temperatures Under Cellular Level 1. A549 cells were seeded in 10 mm dishes, $1 \times 10^8$ cells per dish, and cultured for 12 hours.
2. After step 1 was completed, A549 cells were grouped and treated as follows:

Group 1: the WSN-WT virus solution (virus dose was $10^6$ PFU) prepared in Example 3 was inoculated into the A549 cells, and the medium was changed to virus infection solution one hour after inoculation; the cells were cultured at 37° C., the supernatant was collected at 12, 24, 36, 48, 60 and 72 hours after inoculation, and the virus titer was detected by plaque identification.

Group 2: the WSN-Y385F virus solution (virus dose was $10^6$ PFU) prepared in Example 3 was inoculated into the A549 cells, and the medium was changed to virus infection solution one hour after inoculation; the cells were cultured at 37° C., the supernatant was collected at 12, 24, 36, 48, 60 and 72 hours after inoculation, and the virus titer was detected by plaque identification.

Group 3: the difference between group 3 and group 1 only lies in that the culture temperature was changed from 37° C. to 33° C.

Group 4: the difference between group 4 and group 2 only lies in that the culture temperature was changed from 37° C. to 33° C.

The method for identification of plaque was same as that in Example 3. 10 repetitions were set for each group, and the results were averaged.

Figure 5:
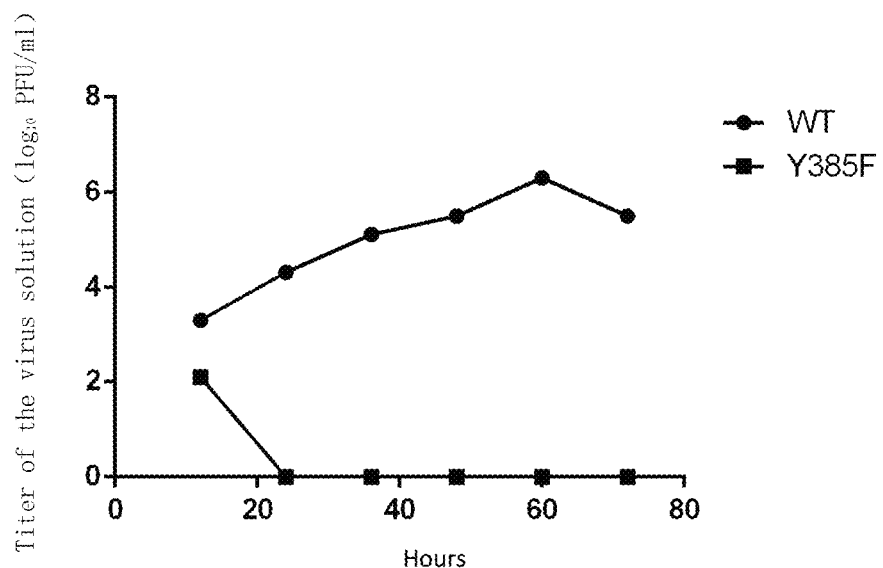
FIG. 5 shows the result of Example 4. (A) 33° C., (B) 37° C.
Figure 5:
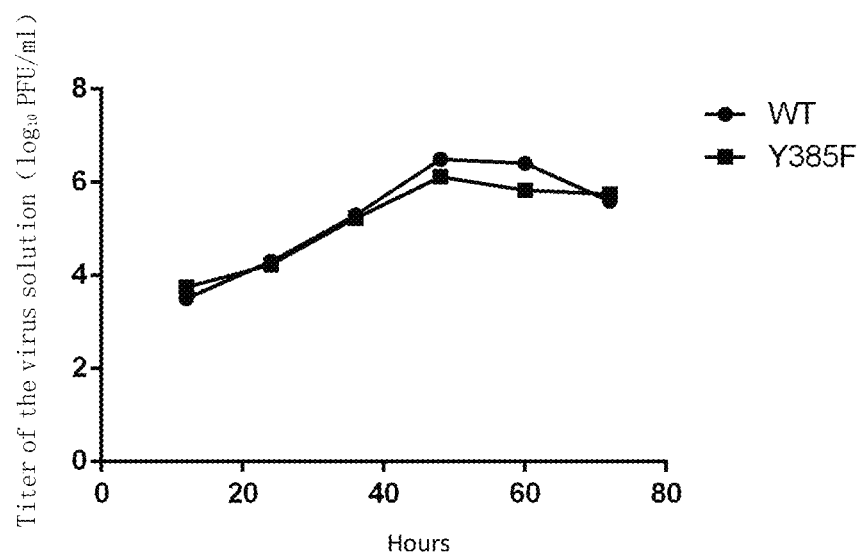

The result was shown in FIG. 5. In FIG. 5, A was the results of group 3 and group 4, and B was the results of group 1 and group 2.

During the culture at 33° C., all the WSN-WT viruses could replicate normally and the virus titer was kept a relatively stable and slowly rising tendency. The virus titer of WSN-Y385F was 0 after 24 hours of culture at 33° C., i.e., WSN-Y385F virus could not replicate at 33° C. During the culture at 37° C., both WSN-WT virus and WSN-Y385F virus could replicate normally and the virus titers of both were kept a relatively stable and slowly rising tendency. The result indicated that WSN-Y385F virus is a temperature-sensitive virus.

Example 5. Difference in Virus Growth Curves at Different Temperatures Under Animal Level 36 6-8 weeks old BALB/c mice with body weight of about 17 g were subjected to ether anesthesia and then randomly divided into three groups, there were 12 mice in each group, and the mice were respectively treated as follows:

Group 1: 50 µl of the WSN-WT virus solution (virus titer was $10^4$ PFU/ml) prepared in Example 3 was inhaled by nasal inhalation;

Group 2: 50 µl of the WSN-Y385F virus solution (virus titer was $10^4$ PFU/ml) prepared in Example 3 was inhaled by nasal inhalation;

Group 3: 50 µl of sterilized PBS buffer was inhaled by nasal inhalation.

After the above treatment was completed, timing was started. The mice were dissected (3 mice in each group at each time point), and lungs and turbinal bones were obtained (temperatures of the lungs and turbinal bones were different, the temperature of the nasal bones was lower, about 33° C., and the temperature of the lungs was higher, about 37° C.) at day 1, day 3, day 5, and day 7, respectively.

0.1 g fresh weight lung or turbinal bone was weighed, 1 ml of ice bathed PBS buffer with pH 7.2 was added, the tissue was homogenated using QIAGEN TissueLyser II (homogenization parameters: 30 cycles/s, in total 4 min), and then centrifuged at 5000 g for 10 min, the supernatant was collected.

The virus titer in the supernatant was detected by plaque identification (the method for identification of plaque was same as that in Example 3).

Figure 6:
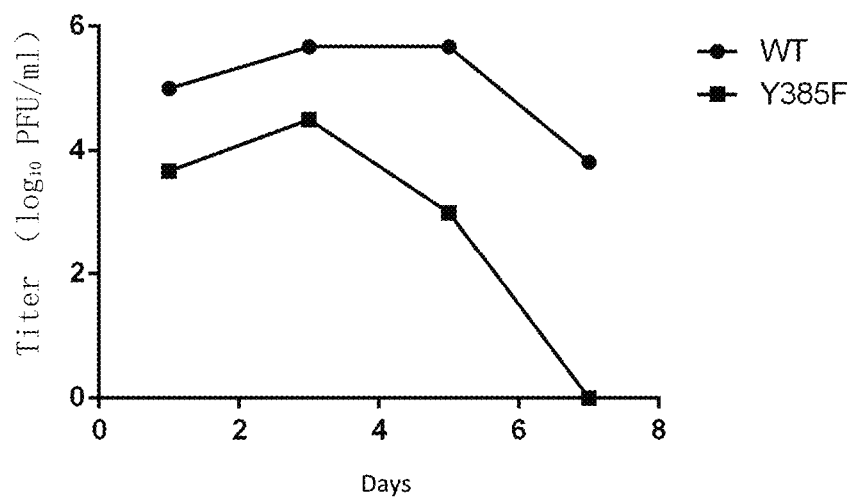
FIG. 6 shows the result of Example 5. (A) lung (37° C.), (B) turbinal bones (33° C.).
Figure 6:
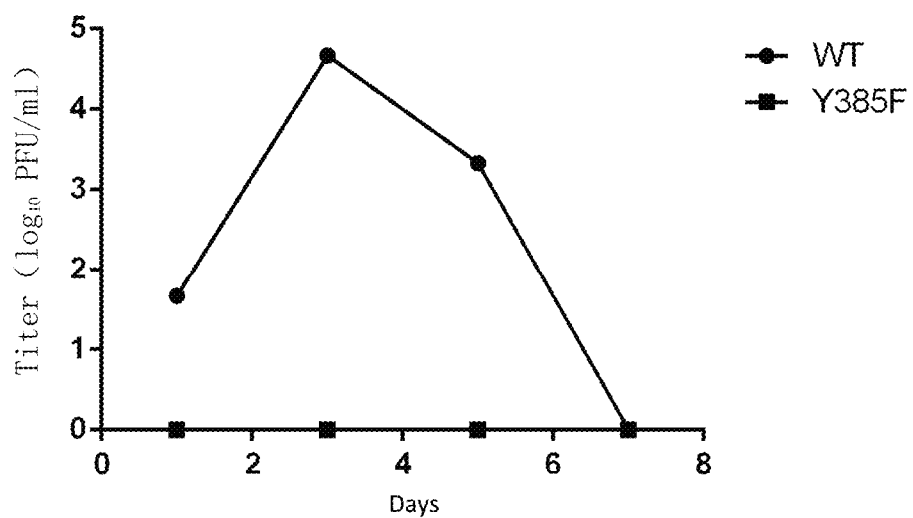

The result was shown in FIG. 6. In FIG. 6, A was the result from the lung, and B was the result from the turbinal bone.

In the urbinal bones, all WSN-WT viruses could replicates normally and the virus titer was kept a relatively stable and slowly descending tendency. In the urbinal bones, the virus titer of WSN-Y385F was 0, that was, WSN-Y385F virus could not replicate at 33° C. In the lungs, both WSN-WT virus and WSN-Y385F virus could replicate normally and the virus titer was kept a relatively stable and slowly descending tendency. The result showed that WSN-Y385F virus is a temperature-sensitive virus.

INDUSTRY APPLICATION

The present invention has great value for the mechanism analysis of infection of influenza virus, prevention and treatment of influenza virus and the like.

The invention claimed is:

1. A recombinant influenza A virus, comprising a genome with a nucleoprotein (NP) in which a codon that encodes a tyrosine residue at a position corresponding to position 385 in SEQ ID NO: 1 is mutated to a codon of that encodes a phenylalanine residue.

2. An influenza A nucleoprotein protein having a phenylalanine residue at a position corresponding to position 385 in SEQ ID NO: 1.

3. An isolated gene encoding the influenza A nucleoprotein of claim 2.

4. A recombinant plasmid comprising the isolated gene of claim 3.

5. A method for preparing a recombinant influenza A virus comprising:
co-transfecting in vitro mammalian cells with plasmid pHH21-PA, plasmid pHH21-PB1, plasmid pHH21-PB2, plasmid pHH21-HA, plasmid pHH21-NA, plasmid pHH21-M, plasmid pHH21-NS, plasmid pcDNA3.0-PA, plasmid pcDNA3.0-PB1, plasmid pcDNA3.0-PB2, recombinant plasmid pHH21-NP-Y385F and recombinant plasmid pcDNA3.0-NP-Y385F, and
then culturing the cells to obtain the recombinant virus.

6. A method of removing a phosphorylation site of a NP protein of influenza A virus comprising mutating an amino acid residue at a position corresponding to position 385 of SEQ ID NO: 1 from a tyrosine to an phenylalanine.

7. A method of preparing an influenza A virus vaccine comprising obtaining the recombinant virus produced in the method of claim 5, formulated in a solution.

8. A method of inducing an immune response in a subject comprising administering the recombinant virus of claim 1 to the subject.

9. An influenza A virus vaccine comprising as an active ingredient the recombinant virus obtained from the method of claim 7.

10. A plasmid combination consisting of the plasmid pHH21-PA, plasmid pHH21-PB1, plasmid pHH21-PB2, plasmid pHH21-HA, plasmid pHH21-NA, plasmid pHH21-M, plasmid pHH21-NS, plasmid pcDNA3.0-PA, plasmid pcDNA3.0-PB1, plasmid pcDNA3.0-PB2, recombinant plasmid pHH21-NP-Y385F and recombinant plasmid pcDNA3.0-NP-Y385F.

11. A kit for preparing a recombinant influenza A virus, comprising the plasmid combination of claim 10.

* * * * *